(12) United States Patent
Darras et al.

(10) Patent No.: US 10,363,379 B2
(45) Date of Patent: Jul. 30, 2019

(54) SAFETY DEVICE FOR A MEDICAMENT CONTAINER

(71) Applicant: Sanofi, Paris (FR)

(72) Inventors: David Darras, Paris (FR); Fabien Canepa, Paris (FR); Bruno Serre, Paris (FR); Jacky Mazzolini, Oyonnax (FR)

(73) Assignee: Sanofi, Paris (FR)

( * ) Notice: Subject to any disclaimer, the term of this patent is extended or adjusted under 35 U.S.C. 154(b) by 154 days.

(21) Appl. No.: 14/914,759

(22) PCT Filed: Aug. 27, 2014

(86) PCT No.: PCT/EP2014/068130
§ 371 (c)(1),
(2) Date: Feb. 26, 2016

(87) PCT Pub. No.: WO2015/028487
PCT Pub. Date: Mar. 5, 2015

(65) Prior Publication Data
US 2016/0206831 A1    Jul. 21, 2016

(30) Foreign Application Priority Data
Aug. 29, 2013    (EP) .................................... 13306179

(51) Int. Cl.
*A61M 5/31*    (2006.01)
*A61M 5/32*    (2006.01)

(52) U.S. Cl.
CPC ........ *A61M 5/3243* (2013.01); *A61M 5/3137* (2013.01); *A61M 5/326* (2013.01); *A61M 2005/3139* (2013.01); *A61M 2005/3264* (2013.01); *A61M 2205/586* (2013.01)

(58) Field of Classification Search
CPC .. A61M 5/3243; A61M 5/3137; A61M 5/326; A61M 5/3135; A61M 2005/3139; A61M 2005/3247
See application file for complete search history.

(56) References Cited

U.S. PATENT DOCUMENTS

| 6,613,022 | B1 | 9/2003 | Doyle |
| 6,623,459 | B1 | 9/2003 | Doyle |
| 7,041,085 | B2 | 5/2006 | Perez et al. |
| 7,101,355 | B2 | 9/2006 | Doyle |
| 7,300,420 | B2 | 11/2007 | Doyle |
| 8,591,463 | B1 | 11/2013 | Cowe |

(Continued)

FOREIGN PATENT DOCUMENTS

| WO | WO 2005/039678 | 5/2005 |
| WO | WO 2006/105006 | 10/2006 |

OTHER PUBLICATIONS

International Search Report and Written Opinion in International Application No. PCT/EP2014/068130, dated Jan. 12, 2014, 9 pages.

(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

A safety device for a medicament container includes a first sheath having a first ledge and a second ledge, a second sheath telescopically arranged with the first sheath and releasably coupled to the first ledge, and a finger flange having at least one resilient clip adapted to engage the second ledge first sheath.

20 Claims, 7 Drawing Sheets

(56) References Cited

U.S. PATENT DOCUMENTS

| | | | |
|---|---|---|---|
| 2002/0099342 A1* | 7/2002 | Zurcher | A61M 25/0631 604/272 |
| 2002/0133122 A1* | 9/2002 | Giambattista | A61M 5/3202 604/198 |
| 2002/0193746 A1 | 12/2002 | Chevallier et al. | |
| 2003/0144607 A1* | 7/2003 | Mathias | A61M 1/0209 600/573 |
| 2007/0179441 A1* | 8/2007 | Chevallier | A61M 5/326 604/110 |
| 2008/0298879 A1* | 12/2008 | Chesak | A61M 35/003 401/133 |
| 2009/0020468 A1* | 1/2009 | Dannenmaier | A61M 1/16 210/232 |
| 2009/0078252 A1* | 3/2009 | Anderson | A61M 15/0045 128/202.22 |
| 2010/0137810 A1* | 6/2010 | Chandrasekaran | A61M 5/326 604/198 |
| 2010/0280316 A1* | 11/2010 | Dietz | A61B 8/12 600/109 |
| 2011/0276026 A1* | 11/2011 | Dowds | A61M 5/3137 604/506 |
| 2012/0046615 A1* | 2/2012 | Koiwai | A61M 5/3243 604/192 |
| 2012/0123349 A1* | 5/2012 | Chun | A61M 5/3257 604/198 |
| 2012/0203186 A1* | 8/2012 | Vogt | A61M 5/3202 604/192 |
| 2013/0053788 A1* | 2/2013 | Dugand | A61M 5/3243 604/198 |
| 2013/0144220 A1* | 6/2013 | Cleathero | A61M 5/3135 604/218 |
| 2013/0220869 A1* | 8/2013 | Klintenstedt | A61M 5/24 206/528 |
| 2015/0057608 A1* | 2/2015 | Hitscherich, Jr. | A61M 5/3137 604/91 |
| 2016/0015891 A1* | 1/2016 | Papiorek | A61M 5/158 604/180 |
| 2016/0076679 A1* | 3/2016 | Mendyk | F16L 37/0841 285/81 |

OTHER PUBLICATIONS

International Search Report on Patentability in International Application No. PCT/EP2014/068130, dated Mar. 1, 2016, 7 pages.

Rote List, "50. Hypophysen-, Hypothalamushormone, andere regulatorische Peptide u. ihre Hemmstoffe," Chapter 50, ed. 2008, 30 pages.

Safety Syringes, Inc., "UltraSafe Passive Needle Guard" Product Specifications, 2 pages.

* cited by examiner

SAFETY DEVICE FOR A MEDICAMENT CONTAINER

CROSS-REFERENCE TO RELATED APPLICATIONS

This application is a U.S. national stage application under 35 USC § 371 of International Application No. PCT/EP2014/068130, filed on Aug. 27, 2014, which claims priority to European Patent Application No. 13306179.6, filed on Aug. 29, 2013, the entire contents of which are incorporated herein by reference.

TECHNICAL FIELD

This disclosure relates to a safety device for a medicament container.

BACKGROUND

Administering an injection is a process which presents a number of risks and challenges for users and healthcare professionals, both mental and physical. Medicament delivery devices typically fall into two categories—manual devices and auto-injectors. In a conventional manual device, manual force is required to drive a medicament through a needle. This is typically done by some form of button/plunger that has to be continuously pressed during the injection. A conventional auto-injector may provide the force for administering the medicament by a spring, and a trigger button or other mechanism may be used to activate the injection.

For use of manual devices and autoinjectors, safety and usability are of the utmost importance. Thus, there remains a need for improved medicament delivery devices which include components or mechanisms for user and patient safety (e.g., to prevent misuse, needlestick, etc.) and enhanced usability (e.g., making the device easier to user before, during and after an injection to improve dose accuracy and compliance).

SUMMARY

Certain embodiments of the present invention provide improved safety devices for medicament containers.

In an exemplary embodiment according to the present invention, a safety device for a medicament container comprises a first sheath having a first ledge and a second ledge, a second sheath telescopically arranged with the first sheath and releasably coupled to the first ledge, and a finger flange having at least one resilient clip adapted to engage the second ledge first sheath.

In an exemplary embodiment the resilient clip comprises a transverse beam extending in a radial inward direction, a longitudinal beam extending from the transverse beam in a proximal direction, a hook comprising a slope surface and a block surface extending from the longitudinal beam in the radial inward direction, wherein during insertion of the outer ledge in a distal direction the second ledge engages the slope surface increasingly deflecting the resilient clip in a radial outward direction, wherein, after the second ledge has passed the slope surface the resilient clip relaxes and the second ledge (36) engages the block surface preventing the second ledge from returning in the proximal direction.

In an exemplary embodiment of the transverse beam comprises a hinge in the shape of a a section with a reduced thickness compared to the rest of the transverse beam.

In an exemplary embodiment the hinge has a thickness of approximately 30% to 70%, in particular 40% to 60% of the thickness of the rest of the transverse beam.

In an exemplary embodiment a protrusion is arranged on one of the finger flange and the first sheath, the protrusion arranged to engage a recess in the other one of the finger flange and the first sheath so as to limit relative rotation between the first sheath and the finger flange.

In an exemplary embodiment, the finger flange comprises a hole adapted to receive the first sheath. The finger flange comprises a central recess disposed adjacent to the hole adapted to receive the second ledge.

In an exemplary embodiment, the finger flange comprises a retaining wall adapted to abut the second ledge. The retaining wall abuts an entire periphery of the second ledge.

In an exemplary embodiment, the finger flange comprises at least one lateral recess disposed adjacent the hole.

In an exemplary embodiment, the finger flange comprises a central portion and at least one support portion extending radially from the central portion. The at least one support portion includes a support surface and wherein the support surface is made from a first material and the support portion is made from a second material, and wherein the first material has a lower durometer than the second material. The support surface may include one or more frictional features.

In an exemplary embodiment the support surface is formed by overmolding or by two-shot injection molding.

In an exemplary embodiment, a radial distance between an outer radial surface and an outer diameter of the hole is approximately 20 mm.

In an exemplary embodiment, the central portion comprises a substantially flat proximal surface and a concave distal surface, and the at least one support portion comprises a substantially flat proximal surface and a concave distal surface.

In an exemplary embodiment, the central portion comprises a substantially flat proximal surface and a substantially flat distal surface, and the at least one support portion comprises a concave proximal surface and a concave distal surface.

In an exemplary embodiment according to the present invention, a medicament delivery device comprises a medicament container and a safety device according to any one of the exemplary embodiments.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Certain embodiments of the present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION

Figure 1:
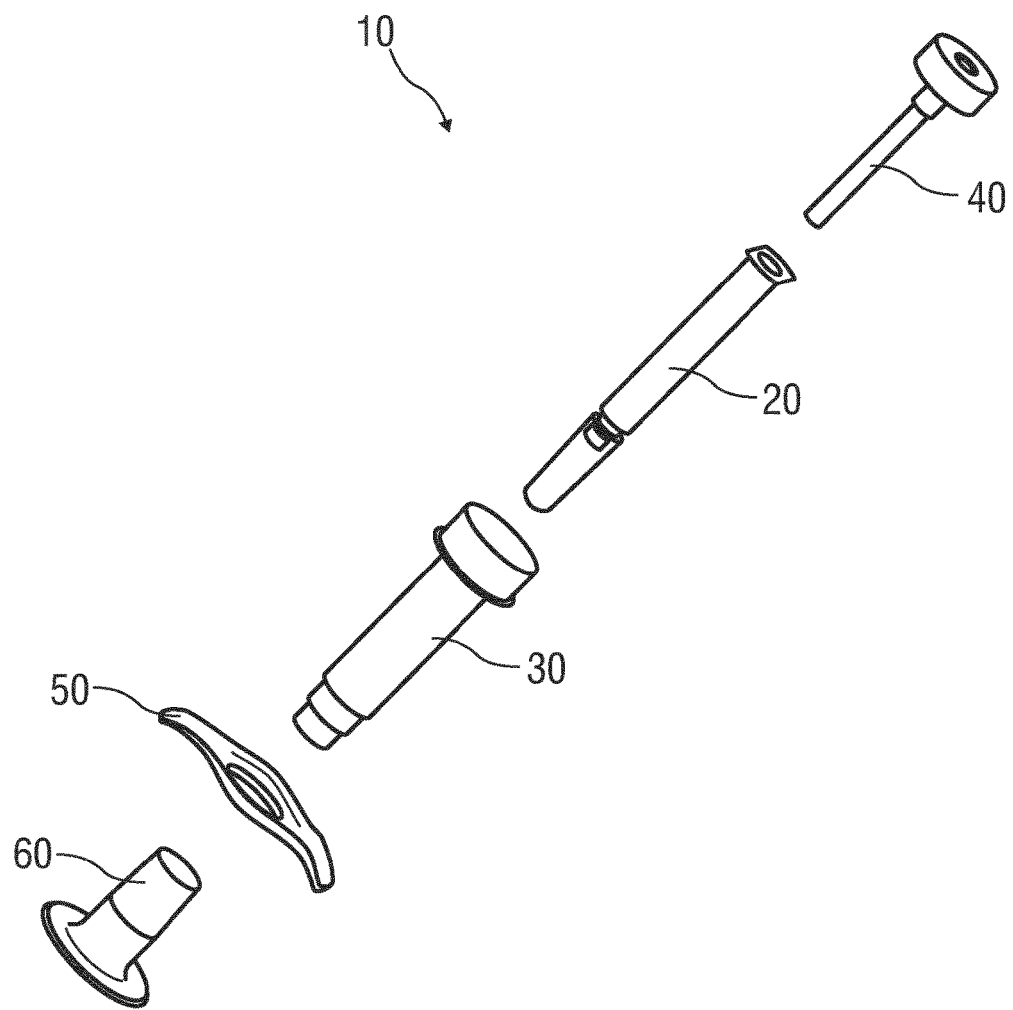
FIG. 1 shows a medicament delivery device according to certain embodiments of the present invention.

FIG. 1 shows a medicament delivery device 10 according to certain embodiments of the present invention. In an exemplary embodiment, the delivery device 10 comprises a medicament container 20, a safety device 30 and a plunger 40. The delivery device 10 may further include a finger flange 50 and/or a cap 60.

Figure 2:
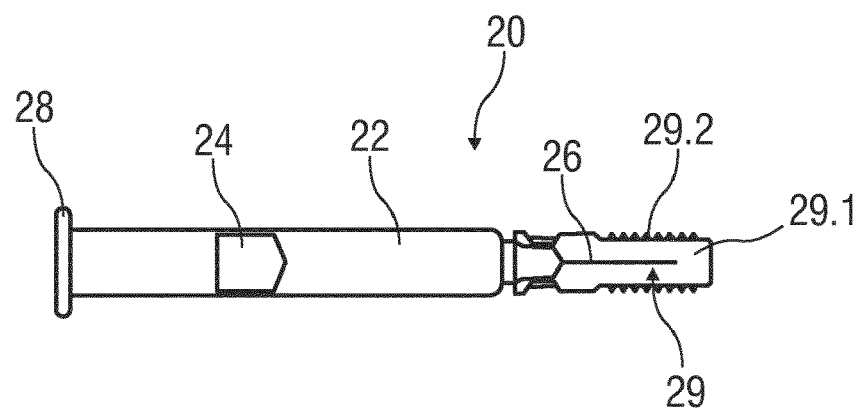
FIG. 2 shows a medicament container according to the present invention.

FIG. 2 shows an exemplary of a medicament container 20 according to the present invention. In the exemplary embodiment, the medicament container 20 includes a barrel 22, a stopper 24 slidably disposed in the barrel 22 and a needle 26 coupled to a distal end of the barrel 22. In an exemplary embodiment, the stopper 24 may be made from a rubber material. A proximal end of the barrel 22 includes a flange 28 which may be fully or partial circular, elliptical, square, rectangular or any other shape. The barrel 22 may be any size (e.g., 0.5 ml, 1 ml, 2 ml, etc.) and be made of any suitable material (e.g., plastic, glass). In an exemplary embodiment, the barrel 22 may be manufactured from Type I clear glass. In an exemplary embodiment, the stopper 24 is made from a rubber material. In an exemplary embodiment, the needle 26 is made from stainless steel. The needle 26 may be any gauge or length.

In an exemplary embodiment, a needle shield 29 may be removably coupled to the distal end of the barrel 22 to cover the needle 26. In an exemplary embodiment, the needle shield 29 may be a sheath 29.1 made of, for example, rubber or elastomer latex.

In another exemplary embodiment, the needle shield 29 may further include a casing 29.2 made of, for example, polypropylene or any other similar material. The casing 29.2 may be disposed partially or entirely on an outer surface of the sheath 29.1. The casing 29.2 may provide further support to the sheath 29.1 to, for example, prevent the needle 26 from bending or puncturing the sheath 29.1. When the needle shield 29 is removed, the needle 26 is exposed.

Figure 3:
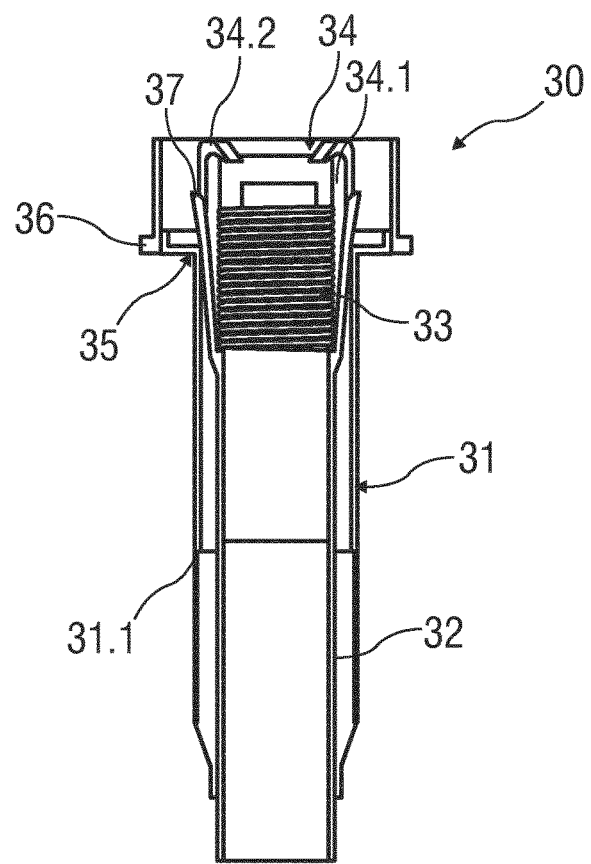
FIG. 3 shows a safety device according to the present invention.

FIG. 3 shows a safety device 30 according to certain embodiments of the present invention. In the exemplary embodiment, the safety device 30 comprises a first sheath 31 arranged telescopically with a second sheath 32, and the sheaths 31, 32 which are biased relative to each other by a spring 33. Prior to use, one of the sheaths is in a retracted position relative to the other sheath, and after use, the one of the sheaths is in an extended position relative to the other sheath to cover the needle 26. In the extended position, the one of the sheaths is locked in the extended position to prevent retraction and uncovering of the needle 26.

In the exemplary embodiment shown in FIG. 3, the first sheath 31 is an outer sheath, and the second sheath 32 is an inner sheath, and the second sheath 32 is movable from the retracted position to the extended position relative to the first sheath 31. The first sheath 31 comprises an open distal end allowing the second sheath 32 to move from the retracted position to the distal position. A proximal end of the first sheath 31 includes an engagement arrangement 34 adapted to engage the flange 28 of the medicament container 20. In an exemplary embodiment, the engagement arrangement 34 includes a support surface 34.1 adapted to abut a distal surface of the flange 28 to prevent distal movement of the medicament container 20 relative to the first sheath 31, and one or more resilient hooks 34.2 adapted to engage the flange 28 to prevent proximal movement of the medicament container 20 relative to the first sheath 31. When the medicament container 20 is inserted into the first sheath 31, the flange 28 causes the resilient hooks 34.2 to deflect until the flange 28 is distal of the hooks 34.2, at which point the hooks 34.2 return to a non-deflected position and can abut a proximal surface of the flange 28.

In an exemplary embodiment, the proximal end of the first sheath 31 includes an inner ledge 35 and an outer ledge 36. The inner ledge 35 may be formed partially or entirely around a proximal opening of the first sheath 31. The outer ledge 36 may be formed partially or entirely around an outer surface of the first sheath 31. As shown in the exemplary embodiment in FIG. 3, the first sheath 31 may have a distal portion having a first outer diameter and a proximal portion having a second outer diameter which is larger than the first outer diameter. The outer ledge 36 may be formed partially or entirely around the larger second outer diameter to provide a support surface for a user's fingers.

In an exemplary embodiment, the second sheath 32 comprises an open distal end allowing the needle 26 to pass through when the second sheath 32 is in the retracted position. A proximal end of the second sheath 32 includes one or more resilient arms 37 adapted to releaseably engage the inner ledge 35 to maintain the second sheath 32 in the retracted position against the force of the spring 33 which biases the second sheath 32 towards the extended position. When the second sheath 32 is in the retracted position, the resilient arms 37 are radially biased to engage the inner ledge 35.

In an exemplary embodiment, the first sheath 31 is made from polycarbonate, the second sheath is made from copolyester, and the spring 33 is made from stainless steel.

Figure 4A:
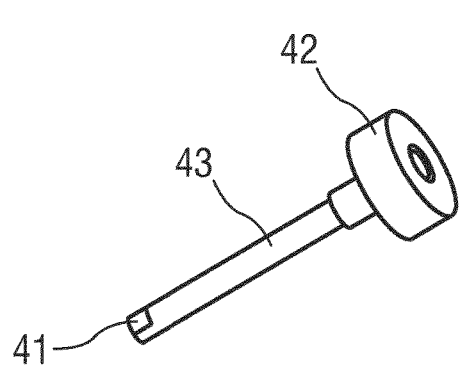
FIGS. 4A and 4B show a plunger according to the present invention.
Figure 4B:
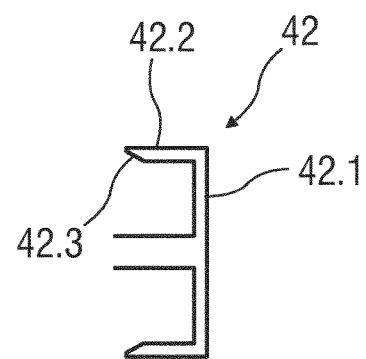

FIGS. 4A and 4B show a plunger 40 according to certain embodiment of the present invention. In the exemplary embodiment, the plunger 40 includes a distal end 41 adapted to engage the stopper 24, a proximal end 42 adapted to be pressed by a user, and a stem 43 connecting the distal and proximal ends 41, 42. FIG. 4B shows a partial cross-section of an exemplary embodiment of the proximal end 42 of the plunger 40. In the exemplary embodiment, the proximal end 42 includes a bearing surface 42.1 adapted to receive a user's finger. The bearing surface 42.1 may be flat (perpendicular relative to a longitudinal axis of the medicament container 20) or have a partially or entirely concave or convex surface. In another exemplary embodiment, the bearing surface 42.1 may have one or more surface elements (e.g., ridges, bumps, etc.) adapted to frictionally engage the user's finger to prevent it from slipping off the bearing surface 42.1 during use. The proximal end 42 further includes a radial surface 42.2 having a distal end that is adapted to engage one or more resilient projections on the first sheath 31 that deflect upon engagement with the radial surface 42.2 to engage the one or more resilient arms 37 on the second sheath 32 when the plunger 40 has been pressed a sufficient distance relative to the medicament container 20. In an exemplary embodiment, the distal end of the radial surface 42.2 may comprise one or more ramps 42.3 adapted to engage the resilient projections such that the resilient rejections resilient arms 37 deflect and disengage the inner ledge 35.

In an exemplary use, when the plunger 40 is pressed a sufficient distance, the ramps 42.3 engage the resilient projections which engage the resilient arms 37 such that the resilient arms 37 deflect and disengage the inner ledge 35. The force of the spring 33 pushes the second sheath 32 distally relative to the first sheath 31 from the retracted position to the extended position. The second sheath 32 is locked in the extended position, because the resilient arms 37 abut a stop surface 31.1 (shown in FIG. 3) on the first sheath 31 preventing the second sheath 32 from moving proximally relative to the first sheath 31 from the extended position.

In an exemplary embodiment, the plunger 40 is made from polypropylene.

In an exemplary embodiment, the safety device 30 and the plunger 40 may be as described in U.S. Patent Application Publication No. 2002/0193746, the entire disclosure of which is expressly incorporated herein by reference.

Figure 5A:
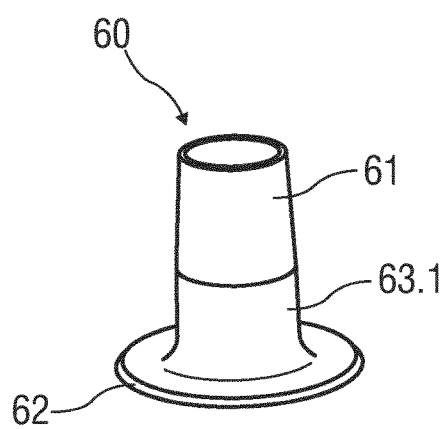
FIGS. 5A and 5B show a cap according to certain embodiments of the present invention.
Figure 5B:
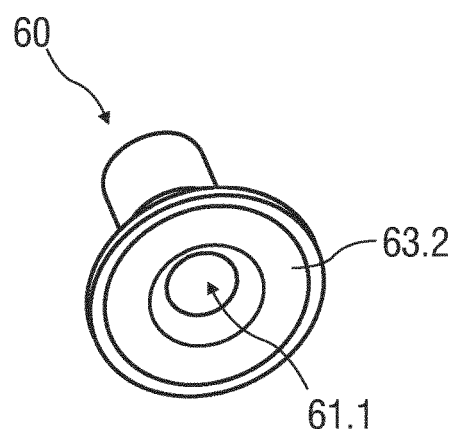

FIGS. 5A and 5B show a cap 60 according to certain embodiment of the present invention. In the exemplary embodiment, the cap 60 comprises cylindrical portion 61 having a first outer diameter and a disc portion 62 having a second outer diameter larger than the second outer diameter. The cylindrical portion 61 includes a thru hole 61.1 adapted to accommodate the needle shield 29. The disc portion 62 may include a thru hole coaxial with the thru hole 61.1 or may include a full or partial cover to fully or partially enclose the thru hole 61.1. When assembled a proximal end of the cylindrical portion 61 may abut a distal end of the first sheath 31.

In an exemplary embodiment, the cap 60 may be made from polypropylene.

In an exemplary embodiment, a gripping surface 63 may be coupled to the cap 60. In the exemplary embodiment, the gripping surface 63 includes a proximal portion 63.1 and a distal portion 63.2. The proximal portion 63.1 may be coupled to all or part of an outer surface of the cylindrical portion 61 of the cap 60 and/or all or part of a proximal surface of the disc portion 62. The distal portion 63.2 may be coupled to all of part of an inner surface of the cylindrical portion 61 of the cap 60 and/or all or part of a distal surface of the disc portion 62. In another exemplary embodiment, the proximal portion 63.1 or the distal portion 63.2 may be disposed partially or entirely around a circumference of the disc portion 62.

In an exemplary embodiment, the gripping surface 63 may be made from a material having a lower durometer than the material comprising the cap 60. In an exemplary embodiment, the gripping surface 63 may be elastomer thermoplastic. The gripping surface 63 may provide an easily grippable and supportive surface for a user to grip to remove the cap 60 from the medicament delivery device 10. In an exemplary embodiment, any part of the gripping surface 63 may include one or more frictional features (e.g., ridges, bumps, etc.) to ensure that the user's fingers do not slip when gripping and removing the cap 60.

Figure 6:
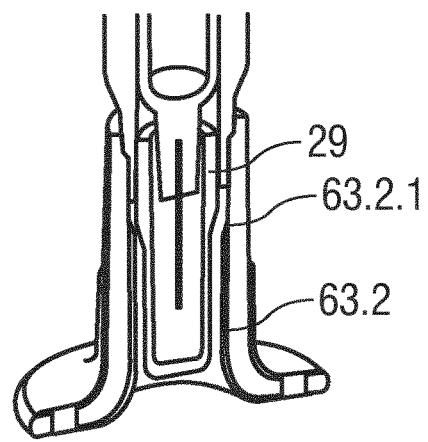
FIG. 6 shows a cap according to certain embodiments of the present invention.

FIG. 6 shows an exemplary embodiment of a cap 60 coupled to the medicament delivery device 10. In the exemplary embodiment, the distal portion 63.2 of the gripping surface 63 is partially disposed on the inner surface of the cylindrical portion 61 of the cap 60. In an exemplary embodiment, a thickness of the distal portion 63.2 may decrease along the length of the inner surface in the proximal direction. A proximal end of the distal portion 63.2 along the length of the inner surface may include a ramp feature 63.2.1 adapted to receive and guide the needle shield 29, e.g., during assembly. The distal portion 63.2 of the gripping surface 63 is adapted to frictionally engage the needle shield 29, such that when the cap 60 is pulled away from the medicament delivery device 10, the needle shield 29 is removed. In another exemplary embodiment, all or part of the distal portion 63.2 may include one or more engagement features (e.g., a barb, a hook, a projection, etc.) adapted to engage the needle shield 29 (or any feature thereof, e.g., a slot, a channel, a recess, etc.) when the needle shield 29 is inserted into the cap 60. In an exemplary embodiment, the distal portion 63.2 may include one or more separate pieces of material. For example, a first piece of material may be disposed on the inner surface of the cylindrical portion 61 and a second piece of material may be disposed on the distal surface of the disc portion 62. A thru-hole 62.1 may be formed in the disc portion 62, e.g., for molding the gripping surface 63.

In an exemplary embodiment, the cap 60 and/or the gripping surface 63 may include one or more indicia for indicating how to remove the cap 60. For example, all or part of the cap 60 may be a first color and all or part of the gripping surface 63 may be a second color different from the first color to signify that this is the needle end of the device 10. In another exemplary embodiment, one or more words or symbols may be disposed on the cap 60 and/or the gripping surface 63. For example, an arrow point in the distal direction and/or the words "PULL" or "DO NOT TWIST" may be disposed on the cap 60 and/or the gripping surface 63.

Figure 7:
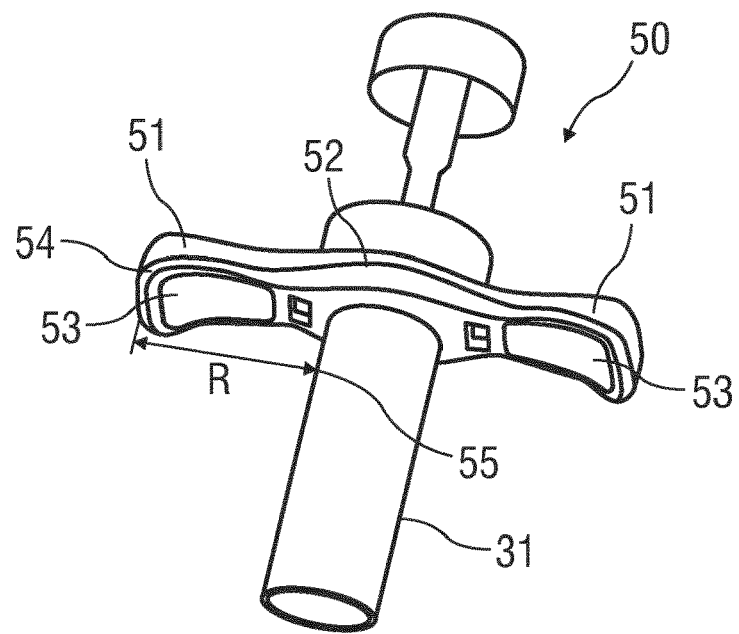
FIG. 7 shows a finger flange according to certain embodiments of the present invention.
Figure 8:
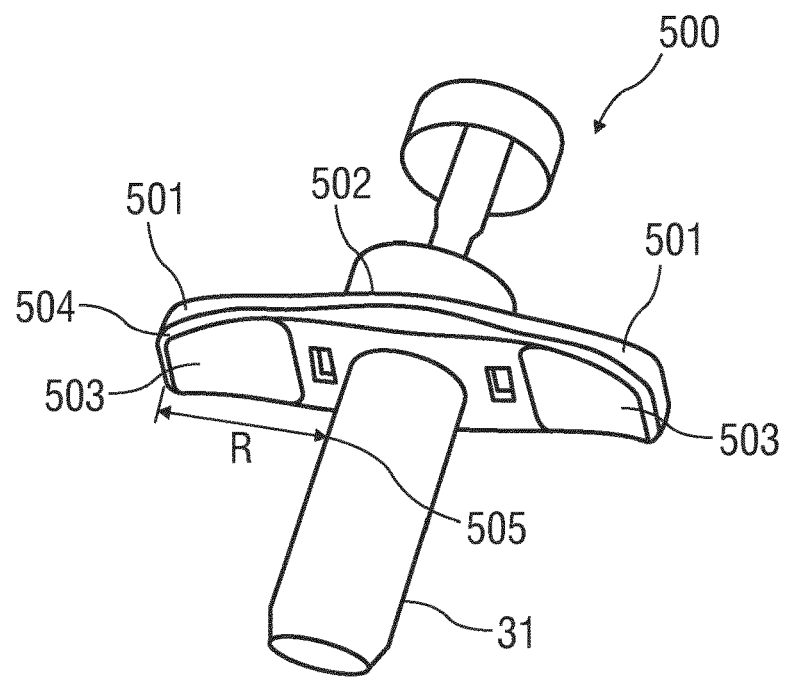
FIG. 8 shows another finger flange according to certain embodiments of the present invention.
Figure 9:
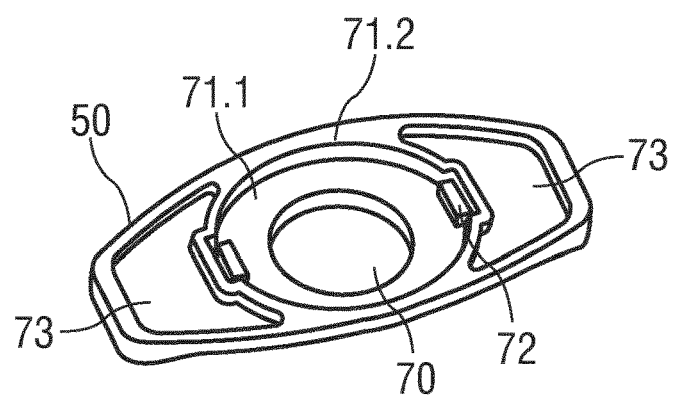
FIG. 9 shows a finger flange according to certain embodiments of the present invention.

FIG. 7 shows a finger flange 50 according to certain embodiment of the present invention. FIG. 8 shows another finger flange 500 according to certain embodiment of the present invention. FIG. 9 shows a proximal view of a finger flange 50/500 according to certain embodiment of the present invention.

As shown in the exemplary embodiment in FIG. 9, a proximal surface of the finger flange 50/500 include a hole 70 adapted to receive the first sheath 31. In an exemplary embodiment, a diameter of the hole 70 is approximately equal to an outer diameter of the first sheath 31. A central recess 71 may be formed around the hole 70 and be adapted to accommodate a proximal portion of the first sheath 31. For example, the central recess 71 may include a bearing surface 71.1 adapted to abut a distal face of the outer ledge 36. The central recess 71 may further include a retaining wall 71.2 adapted to abut at least a portion of the outer ledge 36 to prevent rotation of the first sheath 31 relative to the finger flange 50/500. One or more resilient clips 72 are disposed within or adjacent the central recess 71 and adapted to engage the outer ledge 36. When the finger flange 50/500 is coupled to the first sheath 31, the clips 72 deflect to accommodate the outer ledge 36 and then return to a non-deflected position to engage the outer ledge 36.

In another exemplary embodiment, the bearing surface 71.1 may not be recessed but may be in plane with the proximal surface of the finger flange 50/500. In this exemplary embodiment, the retaining wall 71.2 and the clips 72 may extend proximally from the flat surface.

In an exemplary embodiment, the proximal surface of the finger flange 50/500 may include one or more lateral recesses 73 adjacent the central recess 71. The lateral recesses 73 may be formed to create a hinge effect when supporting the user's fingers. The lateral recesses 73 may further decrease weight of the finger flange 50/500 and reduce constraints on molding.

FIG. 7 shows an exemplary embodiment of the finger flange 50 disposed on the outer sheath 31. In the exemplary embodiment, the finger flange 50 includes one or more support portions 51 extending radially from a central portion 52. The proximal surface of the finger flange 50 is substantially flat and distal surfaces of the support portions 51 and the central portion 52 are concave relative to the proximal surface (e.g., when the finger flange 50 is placed on a flat surface such that the proximal surface engages the flat surface). The support portion 51 may include a support surface 53. In an exemplary embodiment, the support surface 53 may be made, e. g. by overmolding or by two-shot injection molding, from a material having a lower durometer than the material comprising the finger flange 50. In an exemplary embodiment, the support surface 53 may be elastomer thermoplastic. The gripping surface 53 may provide a surface for a user's finger when administering an injection. In an exemplary embodiment, any part of the support surface 53 may include one or more frictional features (e.g., ridges, bumps, etc.) to ensure that the user's fingers do not slip when administering the injection. Likewise, the support surface 53 may be formed without such surface structures. While the exemplary embodiment of the invention shows two support portions 51 extending radially in a wing-like fashion from the central portion 52, those of skill in the art will understand that any number of support portions 51 in any shape, size or dimension may be utilized based on the intended application. For example, a radial distance R between an outer radial surface 54 and an inner radial surface 55 may be approximately 20 mm. However, for use with elderly or arthritic patients, the radial distance may be increased, and the support portions may be larger.

In an exemplary embodiment, the finger flange 50 may be made from polypropylene or acrylonitrile butadiene styrene and the support surfaces 53 may be made from elastomer thermoplastic.

FIG. 8 shows an exemplary embodiment of the finger flange 500 disposed on the outer sheath 31. In the exemplary embodiment, the finger flange 500 includes one or more support portions 501 extending radially from a central portion 502. Proximal and distal surfaces of the support portions 501 are concave, and proximal and distal surfaces of the central portion 502 are substantially flat (e.g., approximately perpendicular to a longitudinal axis of the first sheath 31). The support portion 501 may include a support surface 503. In an exemplary embodiment, the support surface 503 may be made, e. g. by overmolding or by two-shot injection molding, from a material having a lower durometer than the material comprising the finger flange 500. In an exemplary embodiment, the support surface 503 may be elastomer thermoplastic. The gripping surface 503 may provide a surface for a user's finger when administering an injection. In an exemplary embodiment, any part of the support surface 503 may include one or more frictional features (e.g., ridges, bumps, etc.) to ensure that the user's fingers do not slip when administering the injection. Likewise, the support surface 53 may be formed without such surface structures. While the exemplary embodiment of the invention shows two support portions 501 extending radially in a wing-like fashion from the central portion 502, those of skill in the art will understand that any number of support portions 501 in any shape, size or dimension may be utilized based on the intended application. For example, a radial distance R between an outer radial surface 504 and an inner radial surface 505 may be approximately 20 mm. However, for use with elderly or arthritic patients, the radial distance may be increased, and the support portions may be larger.

In an exemplary embodiment, the finger flange 500 may be made from polypropylene or acrylonitrile butadiene styrene and the support surfaces 503 may be made from elastomer thermoplastic.

Figure 10:
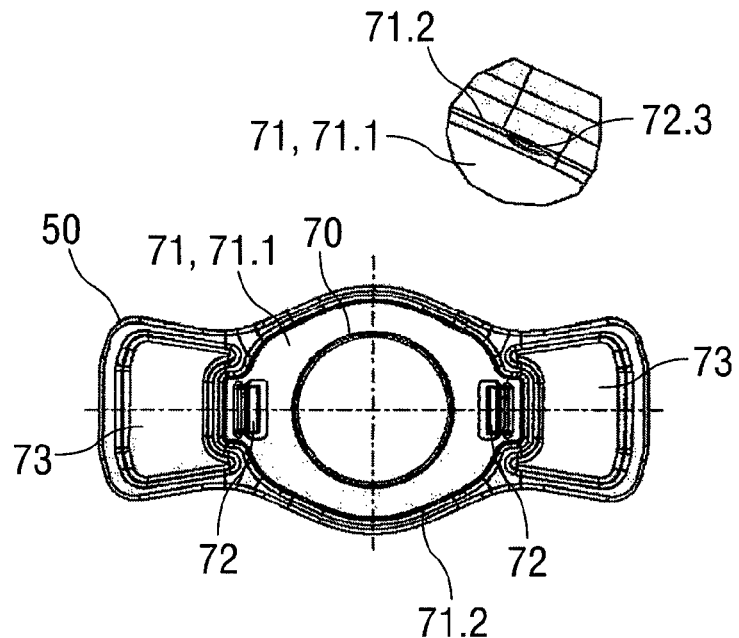
FIG. 10 shows a finger flange according to certain embodiments of the present invention.

FIG. 10 shows a finger flange 50 according to certain embodiments of the present invention. A proximal surface of the finger flange 50 includes a hole 70 adapted to receive the first sheath 31. In an exemplary embodiment, a diameter of the hole 70 is approximately equal to an outer diameter of the first sheath 31. A central recess 71 may be formed around the hole 70 and be adapted to accommodate a proximal portion of the first sheath 31. For example, the central recess 71 may include a bearing surface 71.1 adapted to abut a distal face of the outer ledge 36. The central recess 71 may further include a retaining wall 71.2 adapted to abut at least a portion of the outer ledge 36 to prevent rotation of the first sheath 31 relative to the finger flange 50. One or more resilient clips 72 are disposed within or adjacent the central recess 71 and adapted to engage the outer ledge 36. When the finger flange 50 is coupled to the first sheath 31, the clips 72 deflect to accommodate the outer ledge 36 and then return to a non-deflected position to engage the outer ledge 36.

In another exemplary embodiment, the bearing surface 71.1 may not be recessed but may be in plane with the proximal surface of the finger flange 50. In this exemplary embodiment, the retaining wall 71.2 and the clips 72 may extend proximally from the flat surface.

In an exemplary embodiment, the proximal surface of the finger flange 50 may include one or more lateral recesses 73 adjacent the central recess 71. The lateral recesses 73 may be formed to create a hinge effect when supporting the user's fingers. The lateral recesses 73 may further decrease weight of the finger flange 50 and reduce constraints on molding.

In an exemplary embodiment a protrusion 71.3 is arranged in the retaining wall 71.2 in a manner to engage a respective recess (not illustrated) in the outer ledge 36 so as to avoid and/or limit relative rotation between the first sheath 31 and the finger flange 50.

In another exemplary embodiment the protrusion 71.3 could be arranged in the hole 70 in a manner to engage a respective recess (not illustrated) in the first sheath 31. In the illustrated embodiment the protrusion 71.3 has an arcuate shape. Those skilled in the art will understand that the protrusion 71.3 may take any other form. Likewise, it would be possible to arrange the protrusion 71.3 on the first sheath 31 or on the outer ledge 36 in a manner to let it engage a corresponding recess in the retaining wall 71.2 or in the hole 70.

Figure 11:
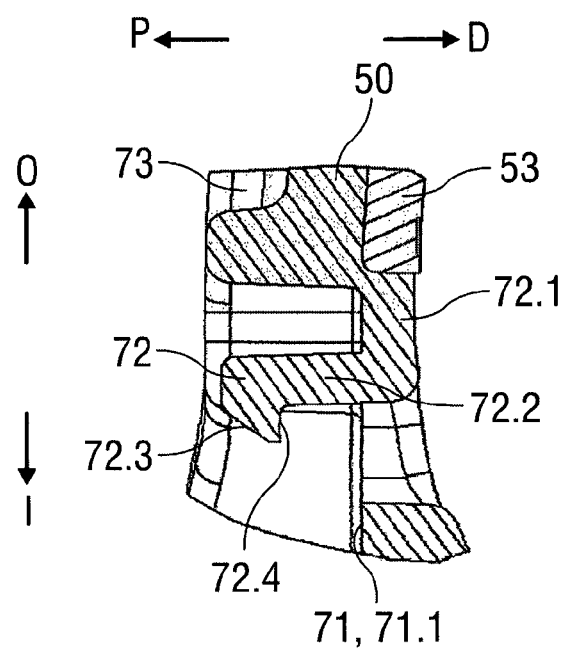
FIG. 11 shows a sectional detail view of a finger flange according to certain embodiments of the present invention.

FIG. 11 shows a sectional detail view of a finger flange 50 according to certain embodiments of the present invention. The resilient clip 72 comprises a transverse beam 72.1 originating from the finger flange 50 and extending in a radial inward direction I. The transverse beam 72.1 may be arranged substantially in parallel with the finger flange 50, i.e. substantially at right angles with respect to the first sheath 31 to be received within the hole 70. The resilient clip 72 furthermore comprises a longitudinal beam 72.2 originating from a radial inward end of the transverse beam 72.1 and extending in a proximal direction P. A hook comprising a slope surface 72.3 and a block surface 72.4 is arranged on the proximal end of the longitudinal beam 72.2 and extends in the radial inward direction I. The slope surface 72.3 allows for inserting the outer ledge 36 of the first sheath 31 in a distal direction D, wherein the outer ledge 36 engages the slope surface 72.3 increasingly deflecting it in a radial outward direction O due to the resilient properties of the transverse beam 72.1 and/or the longitudinal beam 72.2. Once the outer ledge 36 has passed the slope surface 72.3 during insertion the resilient clip 72 relaxes and returns in the radial inward direction I. The distally facing block surface 72.4 thus engages a proximal face of the outer ledge 36 preventing it from returning in the proximal direction P.

Figure 12:
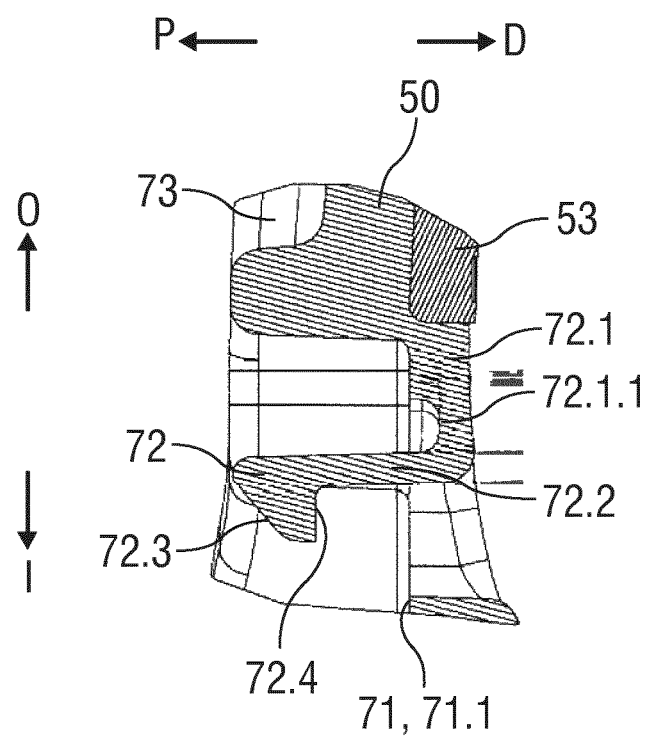
FIG. 12 shows a sectional detail view of a finger flange according to certain embodiments of the present invention.

FIG. 12 shows a sectional detail view of a finger flange 50 according to certain embodiments of the present invention. The embodiment substantially corresponds to the embodiment of FIG. 11. However, the embodiment of FIG. 12 differs from the embodiment of FIG. 11 in that the transverse beam 72.1 comprises a hinge 72.1.1, i.e. a section in which a thickness of the transverse beam 72.1 is reduced with respect to the rest of the transverse beam 72.1. In an exemplary embodiment the hinge 72.1.1 has a thickness of approximately 30% to 70%, in particular 40% to 60% of the thickness of the rest of the transverse beam 72.1. In an exemplary embodiment the hinge 72.1.1 is arranged adjacent the longitudinal beam 72.2.

While exemplary embodiments of the components and/or portions of the cap 60 are described as having certain shapes (e.g., cylinders, discs, etc.) with certain properties that connote a shape (e.g., a diameter, circumference, etc.), those of skill in the art will understand that the cap 60 according to present invention is not limited to any shape or size, but may be adapted for any application or use.

While exemplary embodiments of the present invention are described as being made from certain materials, those of skill in the art will understand that other materials (and/or combinations of materials) may be utilized based on the intended application or use.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu -Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

REFERENCES 10 medicament delivery device
20 medicament container
22 barrel
24 stopper
26 needle
28 flange
29 needle shield
29.1 sheath
29.2 casing
30 safety device
31 first sheath
31.1 stop surface
32 second sheath
33 spring
34 engagement arrangement
34.1 support surface
34.2 resilient hook
35 inner ledge
36 outer ledge
37 resilient arm
40 plunger
41 distal end
42 proximal end
42.1 bearing surface
42.2 radial surface
42.3 ramp
43 stem
50 finger flange
51 support portion
52 central portion
53 support surface
54 outer radial surface
55 inner radial surface
60 cap
61 cylindrical portion
61.1 thru hole
62 disc portion
62.1 thru hole
63 gripping surface
63.1 proximal portion
63.2 distal portion
63.2.1 ramp feature
70 hole
71 central recess
71.1 bearing surface
71.2 retaining wall
71.3 protrusion
72 resilient clip
72.1 transverse beam
72.1.1 hinge
72.2 longitudinal beam
72.3 slope surface
72.4 block surface
73 lateral recess
500 finger flange
501 support portion
502 central portion
503 support surface
504 outer radial surface
505 inner radial surface
D distal direction
I radial inward direction
O radial outward direction
P proximal direction
R radial distance

The invention claimed is:

1. A medicament delivery device comprising:
a medicament container carrying a needle; and
a safety device comprising:
a first sheath through which the needle is movable in a distal direction to enter the safety device, the first sheath comprising a first ledge and a second ledge,
a second sheath telescopically arranged with the first sheath and releasably coupled to the first ledge of the first sheath, and
a finger flange comprising at least one resilient clip adapted to engage the second ledge of the first sheath, the at least one resilient clip comprising:
a transverse beam extending in a radially inward direction relative to a longitudinal axis of the first sheath,
a longitudinal beam extending from the transverse beam in a proximal direction opposite to the distal direction, and
a hook comprising a slope surface and a block surface extending from the longitudinal beam in the radially inward direction,
wherein the second ledge is configured to engage the slope surface such that the at least one resilient clip increasingly deflects in a radially outward direction relative to the longitudinal axis of the first sheath during insertion of the second ledge in the distal direction into the finger flange, and
wherein the second ledge is configured to engage the block surface after the second ledge has passed the slope surface such that the block surface prevents the second ledge from moving in the proximal direction.

2. A safety device for a medicament container, the safety device comprising:
a first sheath through which a needle carried by the medicament container is movable in a distal direction to enter the safety device, the first sheath comprising a first ledge and a second ledge, a second sheath telescopically arranged with the first sheath and releasably coupled to the first ledge of the first sheath; and a finger flange comprising at least one resilient clip adapted to engage the second ledge of the first sheath, the at least one resilient clip comprising:

a transverse beam extending in a radially inward direction relative to a longitudinal axis of the first sheath, a longitudinal beam extending from the transverse beam in a proximal direction opposite to the distal direction, and a hook comprising a slope surface and a block surface extending from the longitudinal beam in the radially inward direction, wherein the second ledge is configured to engage the slope surface such that the at least one resilient clip increasingly deflects in a radially outward direction relative to the longitudinal axis of the first sheath during insertion of the second ledge in the distal direction into the finger flange, and wherein the second ledge is configured to engage the block surface after the second ledge has passed the slope surface such that the block surface prevents the second ledge from moving in the proximal direction.

3. The safety device of claim 2, wherein the transverse beam comprises a hinge with a reduced thickness compared to a thickness of a remaining portion of the transverse beam.

4. The safety device of claim 3, wherein the reduced thickness of the hinge is approximately 30% to 70% of the thickness of the remaining portion of the transverse beam.

5. The safety device of claim 2, wherein a protrusion is arranged on one of the finger flange and the first sheath, the protrusion arranged to engage a recess in the other of the finger flange and the first sheath so as to limit relative rotation between the first sheath and the finger flange.

6. The safety device of claim 2, wherein the finger flange comprises a hole adapted to receive the first sheath.

7. The safety device of claim 6, wherein the finger flange comprises a central recess disposed adjacent to the hole adapted to receive the second ledge.

8. The safety device of claim 6, wherein the finger flange comprises at least one lateral recess disposed adjacent the hole.

9. The safety device of claim 2, wherein the finger flange comprises a retaining wall adapted to abut the second ledge.

10. The safety device of claim 9, wherein the retaining wall abuts an entire periphery of the second ledge.

11. The safety device of claim 2, wherein the finger flange comprises a central portion and at least one support portion extending radially from the central portion.

12. The safety device of claim 11, wherein the at least one support portion includes a support surface, and wherein the support surface is made from a first material and the support portion is made from a second material, and wherein the first material has a lower durometer than the second material.

13. The safety device of claim 12, wherein the support surface includes one or more frictional features.

14. The safety device of claim 12, wherein the support surface is formed by overmolding or by two-shot injection molding.

15. The safety device of claim 6, wherein a radial distance between an outer radial surface of the finger flange and an outer diameter of the hole is approximately 20 mm.

16. The safety device of claim 11, wherein the central portion comprises a substantially flat proximal surface and a concave distal surface.

17. The safety device of claim 16, wherein the at least one support portion comprises a substantially flat proximal surface and a concave distal surface.

18. The safety device of claim 11, wherein the central portion comprises a substantially flat proximal surface and a substantially flat distal surface.

19. The safety device of claim 18, wherein the at least one support portion comprises a concave proximal surface and a concave distal surface.

20. The safety device of claim 1, wherein the hook is a first hook, and wherein the first sheath further comprises a support surface configured to inhibit movement of the medicament container relative to the first sheath in the distal direction and a second hook configured to inhibit movement of the medicament container relative to the first sheath in the proximal direction.

* * * * *